(12) United States Patent
Masuda

(10) Patent No.: US 11,344,240 B2
(45) Date of Patent: May 31, 2022

(54) ELECTRODE CATHETER

(71) Applicant: Japan Lifeline Co., Ltd., Tokyo (JP)

(72) Inventor: Takuya Masuda, Tokyo (JP)

(73) Assignee: Japan Lifeline Co., Ltd., Tokyo (JP)

( * ) Notice: Subject to any disclaimer, the term of this patent is extended or adjusted under 35 U.S.C. 154(b) by 339 days.

(21) Appl. No.: 16/534,618

(22) Filed: Aug. 7, 2019

(65) Prior Publication Data

US 2019/0357790 A1 Nov. 28, 2019

Related U.S. Application Data

(63) Continuation of application No. PCT/JP2017/034228, filed on Sep. 22, 2017.

(30) Foreign Application Priority Data

Mar. 7, 2017 (JP) .............................. JP2017-043343

(51) Int. Cl.
| | | |
|---|---|---|
| *A61B 5/283* | (2021.01) | |
| *A61B 5/00* | (2006.01) | |
| *A61B 5/287* | (2021.01) | |
| *A61B 18/14* | (2006.01) | |

(52) U.S. Cl.
CPC .............. *A61B 5/283* (2021.01); *A61B 5/287* (2021.01); *A61B 5/6852* (2013.01); *A61B 18/1492* (2013.01); *A61B 2562/0209* (2013.01)

(58) Field of Classification Search
CPC ......... A61B 5/293; A61B 5/28; A61B 5/6852; A61B 18/1492; A61B 2562/0209
See application file for complete search history.

(56) References Cited

U.S. PATENT DOCUMENTS

| 2004/0097965 A1* | 5/2004 | Gardeski | A61M 25/0021 |
| | | | 606/129 |
| 2013/0304062 A1* | 11/2013 | Chan | A61B 18/1492 |
| | | | 606/41 |
| 2015/0057655 A1* | 2/2015 | Osypka | A61B 18/1492 |
| | | | 606/41 |

FOREIGN PATENT DOCUMENTS

| CN | 1935099 | 3/2007 |
| JP | 2013-017693 | 1/2013 |

* cited by examiner

*Primary Examiner* — Linda C Dvorak
*Assistant Examiner* — Annabeth E Rodriguez
(74) *Attorney, Agent, or Firm* — Muramatsu & Associates

(57) ABSTRACT

It is an object to provide an electrode catheter in which, when a rotational operation portion is operated, the rotational operation portion and an operating wire do not interfere with a lead wire, do not generate noise during the operation, and do not cause damage or breakage of the lead wire even when the operation is repeated. An electrode catheter according to the present invention includes a tube member 10, a handle 20 having a rotational operation portion 23, electrodes 31 attached to the tube member 10, lead wires 41, an electrode connector 50, and operating wires 71 and 72. A proximal end portion 12 of the tube member 10 is inserted from a distal end of the handle 20 to an inside of the handle 20, and extends in the inside of the handle 20 in the proximal end direction beyond the rotational operation portion 23. Side holes 111 and 115 are formed in a pipe wall of the proximal end portion 12 of the tube member 10. Proximal end portions of the operating wires 71 and 72 pass through the side holes and extend to the outside of the tube member 10. Proximal ends of the operating wires 71 and 72 are fixed to wire fasteners 231 and 232.

4 Claims, 11 Drawing Sheets

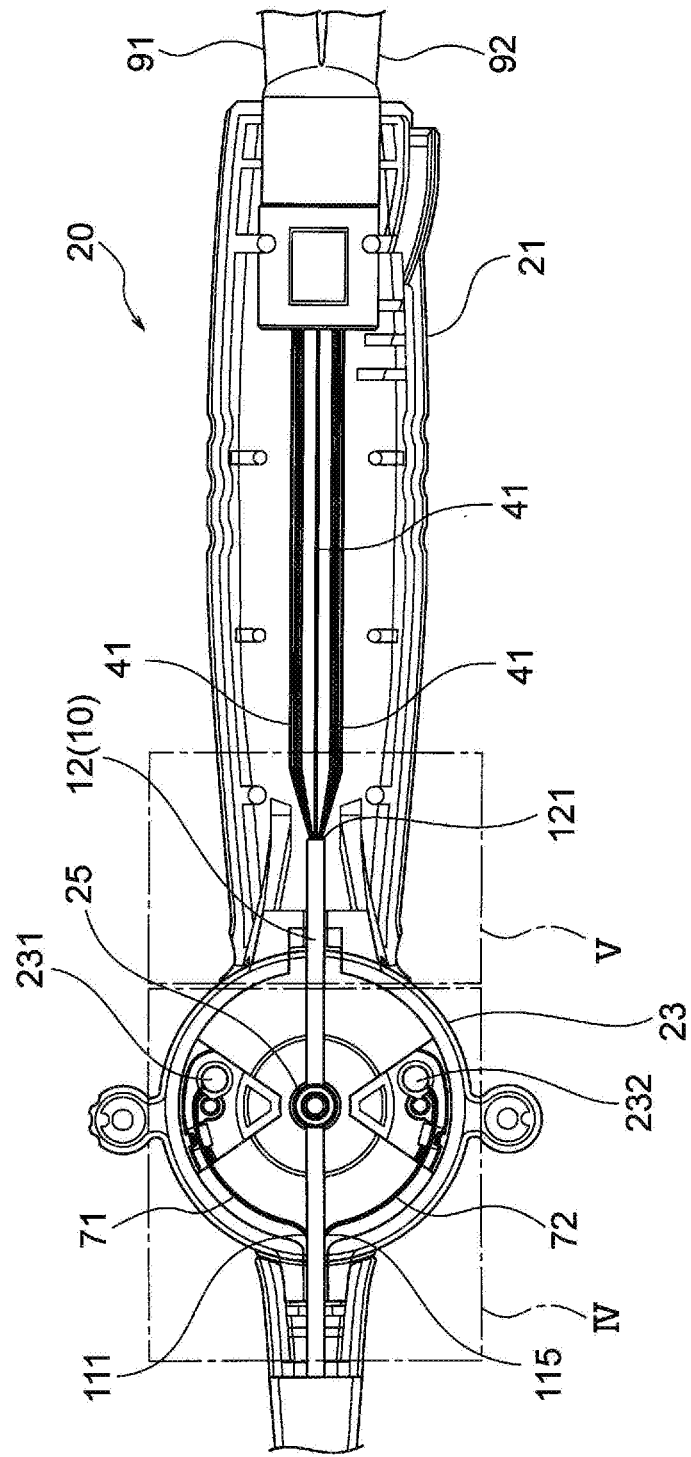

ELECTRODE CATHETER

This is a continuation of International Application No. PCT/JP2017/034228 filed Sep. 22, 2017 which claims the benefit of priority of Japanese Patent Application No. 2017-043343, filed Mar. 7, 2017, the entire contents of which are incorporated herein by reference.

TECHNICAL FIELD

The present invention relates to an electrode catheter.

BACKGROUND ART

In existing electrode catheters, a proximal end portion of a tube member, in an inside of which an operating wire for performing an operation of deflecting a distal end thereof and a lead wire of an electrode extend, is inserted from a distal end side of a handle to an inside of the handle, and the operating wire and the lead wire are caused to extend out to the inside of the handle from a proximal end of the tube member that opens in the vicinity of a distal end of the handle. Here, a proximal end of the operating wire is fixed to a wire fastener of a rotation plate (a rotational operation portion) for a distal-end deflecting operation, a proximal end portion of the lead wire passes through one surface side or the other surface side of the rotational operation portion and extends in the inside of the handle, and a proximal end of the lead wire is connected to an electrode connector that is located on a proximal end side of the rotational operation portion (see PTL 1 listed below).

Moreover, recently, an electrode catheter that includes a mechanism for irrigating a distal end electrode with a liquid, such as saline, has been proposed by the present applicant and others (see PTL 2 listed below). In a tube member that constitutes the electrode catheter described in PTL 2, a central lumen (an irrigation lumen) that serves as a liquid flow path is formed, and, an injection pipe for supplying a liquid to the irrigation lumen is connected to a proximal end of the tube member that is located in the vicinity of the distal end of the handle. The injection pipe extends in an inside of the handle and extends to the outside of the handle from a proximal end portion of the handle.

CITATION LIST

Patent Literature

PTL 1: Japanese Unexamined Patent Application Publication No. 2013-17693
PTL 2: Japanese Unexamined Patent Application Publication No. 2013-202207

SUMMARY OF INVENTION

Technical Problem

Regarding the electrode catheter described in PTL 1, when the rotational operation portion is operated, the rotational operation portion and the operating wire may interfere with the lead wire and noise may be generated, and the lead wire may become damaged (abraded) or may break when the operation is repeated.

Regarding the electrode catheter described in PTL 2, when the rotational operation portion is operated, the rotational operation portion, the operating wire, and the lead wire may interfere with the injection pipe, the injection pipe may kink, and the lumen of the injection pipe may collapse and the flowing characteristics of a liquid may be impaired.

The present invention has been made under the foregoing circumstances. An object of the present invention is to provide an electrode catheter in which, when an operation mechanism, such as a rotational operation portion, for a distal-end deflecting operation is operated, the operation mechanism and an operation wire do not interfere with a lead wire, do not generate noise during the operation, and do not cause damage or breakage of the lead wire even when the operation is repeated.

Another object of the present invention is to provide an electrode catheter in which a tube that has high strength, that does not kink, and whose lumen does not collapse even if the tube receives interference from an operation mechanism for a distal-end deflecting operation, an operating wire, and a lead wire when the operation mechanism is operated extends in an inside of a handle, and thereby a path in the inside of the handle is reliably maintained.

Solution to Problem (1) An electrode catheter of the present invention includes: an insulating tube member that has a flexible portion at a distal end thereof;

a handle that is attached to a proximal end portion of the tube member and that includes an operation mechanism for a distal-end deflecting operation;

at least one electrode (distal end electrode and/or ring-shaped electrode) that is attached to the distal end and/or an outer periphery of a distal end part of the tube member;

at least one lead wire whose distal end is connected to the electrode and that extends in an inside of the tube member along an axial direction;

an electrode connector that is disposed at an outside of the handle or is incorporated in the handle and that has a terminal to which a proximal end of the lead wire is connected; and at least one operating wire whose distal end is fixed to the electrode (distal end electrode) attached to the distal end of the tube member or to a distal end portion of the tube member, that extends in the inside of the tube member along the axial direction, and that is operable to be pulled as a proximal end thereof is fixed to an constituent element of the operation mechanism, in which the proximal end portion of the tube member is inserted from a distal end of the handle to an inside of the handle, and extends in the inside of the handle in a proximal end direction beyond a fixing position on the constituent element of the operation mechanism where the proximal end of the operating wire is fixed, in which at least one side hole that opens in an outer peripheral surface of the tube member is formed in a pipe wall of the proximal end portion of the tube member on a distal end side of the fixing position on the constituent element of the operation mechanism where the proximal end of the operating wire is fixed, and in which the proximal end portion of the operating wire passes through the side hole and extends to an outside of the tube member.

With the electrode catheter having such a structure, the proximal end portion of the tube member extends in the inside of the handle in the proximal end direction beyond the fixing position on the constituent element of the operation mechanism where the proximal end of the operating wire is fixed. Thus, at least a part of each of the lead wires in the inside of the handle that is located in a region from the distal end of the handle to the fixing position where the proximal end of the operating wire is fixed is protected by the tube member. Therefore, each of the lead wires does not receive interference from the operating wire.

Moreover, the proximal end portion of the operating wire is caused to pass through the side hole, which is formed in the proximal end portion of the tube member, and to extend to the outside of the tube member (the inside of the handle). Therefore, it is possible to fix the proximal end of the operating wire to the constituent element of the operation mechanism.

(2) In the electrode catheter of the present invention, preferably, the operation mechanism is a rotational operation portion that includes a wire fastener and that is used for the distal-end deflecting operation, the proximal end of the operating wire is fixed to the wire fastener of the rotational operation portion, and the proximal end portion of the tube member is inserted from the distal end of the handle to the inside of the handle and extends in the inside of the handle in the proximal end direction beyond the rotational operation portion.

With the electrode catheter having such a structure, the proximal end portion of the tube member extends in the inside of the handle in the proximal end direction beyond the rotational operation portion. Thus, at least a part of each of the lead wires in the inside of the handle that is located in a region from the distal end of the handle to the proximal end of the rotational operation portion is protected by the tube member. Therefore, each of the lead wires does not receive interference from the rotational operation portion and the operating wire.

Moreover, the proximal end portion of the operating wire is caused to pass through the side hole formed in the proximal end portion of the tube member and to extend to the outside of the tube member (the inside of the handle). Therefore, although the proximal end portion of the tube member extends in the proximal end direction beyond the rotational operation portion, it is possible to fix the proximal end of the operating wire to the wire fastener of the rotational operation portion.

(3) In the electrode catheter of the present invention, preferably, a proximal end of the tube member is located in the inside of the handle, and a proximal end portion of the lead wire extends to the outside of the tube member from the proximal end of the tube member.

With the electrode catheter having such a structure, the proximal end of the tube member is on the proximal end side of the fixing position on the constituent element of the operation mechanism where the proximal end of the operating wire is fixed in the electrode catheter of (1) described above, and is on the proximal end side of the rotational operation portion in the electrode catheter of (2) described above. Therefore, when the operation mechanism (the rotational operation portion) is operated, the proximal end portion of the lead wire, which extends out from the proximal end of the tube member to the inside of the handle, does not receive interference from the operation mechanism (the rotational operation portion) and the operating wire.

(4) In the electrode catheter of the present invention, preferably, the proximal end portion of the tube member extends to the outside of the handle, at least one side hole that opens in the outer peripheral surface of the tube member is formed in a pipe wall of a part of the proximal end portion of the tube member extending in the inside of the handle on a proximal end side of the fixing position on the constituent element of the operation mechanism where the proximal end of the operating wire is fixed, and a proximal end portion of the lead wire passes through the side hole and extends to the outside of the tube member.

With the electrode catheter having such a structure, the proximal end portion of the tube member is inserted from the distal end of the handle to the inside of the handle, extends in the inside of the handle in the proximal end direction, and extends to the outside of the handle. Therefore, it is possible to reliably maintain paths (an insertion path of a guide wire and the like and a liquid flow path) in the inside of the handle.

Moreover, the tube member, whose proximal end portion extends in the inside of the handle, is a member that constitutes a catheter shaft on the distal end side of the handle and has high strength. Therefore, when the operation mechanism (the rotational operation portion) is operated, even if the tube member receives interference from the operation mechanism (the rotational operation portion), the operating wire, and the lead wire, the proximal end portion of the tube member does not kink and the lumen does not collapse.

Moreover, the proximal end portion of the lead wire is caused to pass through the side hole, which is formed in the proximal end portion of the tube member, and to extend to the outside of the tube member. Therefore, although the proximal end portion of the tube member extends to the outside of the handle, it is possible to cause the proximal end portion of the lead wire to extend out to the inside of the handle.

Moreover, the side hole for causing the proximal end portion of the lead wire to extend out is formed in the pipe wall of the proximal end portion of the tube member on the proximal end side of the fixing position on the constituent element of the operation mechanism where the proximal end of the operating wire is fixed. Therefore, when the operation mechanism (the rotational operation portion) is operated, the proximal end portion of the lead wire, which extends out from the side hole, does not receive interference from the operating wire.

(5) In the electrode catheter of (4) described above, preferably, the tube member has a multi-lumen structure that includes a guide wire lumen, and a guide wire connector that has a port that communicates with the guide wire lumen is connected to a proximal end of the tube member.

With the electrode catheter having such a structure, the guide wire connector is connected to the proximal end of the tube member that is located outside of the handle. Therefore, it is possible to reliably maintain an insertion path of a guide wire that leads from the port of the guide wire connector to a distal end opening of the guide wire lumen of the tube member. Thus, it is possible to insert the electrode catheter to a target region along the guide wire.

Moreover, the tube member that has a multi-lumen structure and that constitutes a catheter shaft on the distal end side of the handle has high strength. Therefore, when the operation mechanism (the rotational operation portion) is operated, even if the tube member receives interference from the operation mechanism (the rotational operation portion), the operating wire, and the lead wire, the proximal end portion of the tube member does not kink and the lumen does not collapse, and the insertion characteristics of the guide wire are not impaired due to a distal-end deflecting operation.

(6) In the electrode catheter of (4) described above, preferably, the tube member has a multi-lumen structure that includes an irrigation lumen, and a liquid injection pipe that communicates with the irrigation lumen is connected to a proximal end of the tube member.

With the electrode catheter having such a structure, the liquid injection pipe is connected to the proximal end of the tube member that is located outside of the handle. Therefore, it is possible to reliably maintain a liquid flow path that leads from the injection pipe to the irrigation lumen of the tube member. Thus, it is possible to irrigate the distal end electrode and the like with a liquid from the injection pipe.

Moreover, the tube member that has a multi-lumen structure and that constitutes a catheter shaft on the distal end side of the handle has high strength. Therefore, when the operation mechanism (the rotational operation portion is operated, even if the tube member receives interference from the operation mechanism (the rotational operation portion), the operating wire, and the lead wire, the proximal end portion of the tube member does not kink and the lumen does not collapse, and the flowing characteristics of a liquid are not impaired due to a distal-end deflecting operation.

Advantageous Effects of Invention

With the electrode catheter according to the present application, when the operation mechanism for a distal-end deflecting operation is operated, the lead wire that constitutes the electrode catheter does not receive interference from the operation mechanism and the operating wire, noise is not generated during the operation, and damage or breakage of the lead wire does not occur even when such an operation is repeated. Moreover, although the proximal end portion of the tube member extends in the proximal end direction beyond the fixing position on the constituent element of the operation mechanism where the proximal end of the operating wire is fixed, it is possible to fix the proximal end of the operating wire to the constituent element of the operation mechanism.

With the electrode catheter according to the present application, when the rotational operation portion is operated, the lead wire that constitutes the electrode catheter does not receive interference from the rotational operation portion and the operating wire, noise is not generated during the operation, and damage or breakage of the lead wire does not occur even when such an operation is repeated. Moreover, although the proximal end portion of the tube member extends in the proximal end direction beyond the rotational operation portion, it is possible to fix the proximal end of the operating wire to the wire fastener of the rotational operation portion.

With the electrode catheter according to the present application, further, the proximal end portion of the lead wire, which extends out from the proximal end of the tube member to the inside of the handle, does not receive interference from the operation mechanism (the rotational operation portion) and the operating wire.

With the electrode catheter according to the present application, further, with the proximal end portion of the tube member that extends to the inside of the handle, it is possible to reliably maintain paths (an insertion path of a guide wire and the like and a liquid flow path) that pass through the inside of the handle. Moreover, when the operation mechanism (the rotational operation portion) is operated, even if the proximal end portion of the tube member that extends to the inside of the handle receive interference from the operation mechanism (the rotational operation portion), the operating wire, and the lead wire, the proximal end portion does not kink and the lumen does not collapse. Moreover, although the proximal end portion of the tube member extends to the outside of the handle, it is possible to cause the proximal end portion of the lead wire to extend out to the inside of the handle.

With the electrode catheter according to the present application, further, it is possible to insert the electrode catheter to a target region along the guide wire. Moreover, the insertion characteristics of the guide wire are not impaired due to a distal-end deflecting operation.

With the electrode catheter according to the present application, further, it is possible to irrigate the distal end electrode and the like with a liquid from the injection pipe. Moreover, the flowing characteristics of a liquid are not impaired due to a distal-end deflecting operation.

BRIEF DESCRIPTION OF DRAWINGS

FIG. 3 is a plan view illustrating an inside of a handle that constitutes the electrode catheter illustrated in FIG. 1.

DESCRIPTION OF EMBODIMENTS

Figure 1:
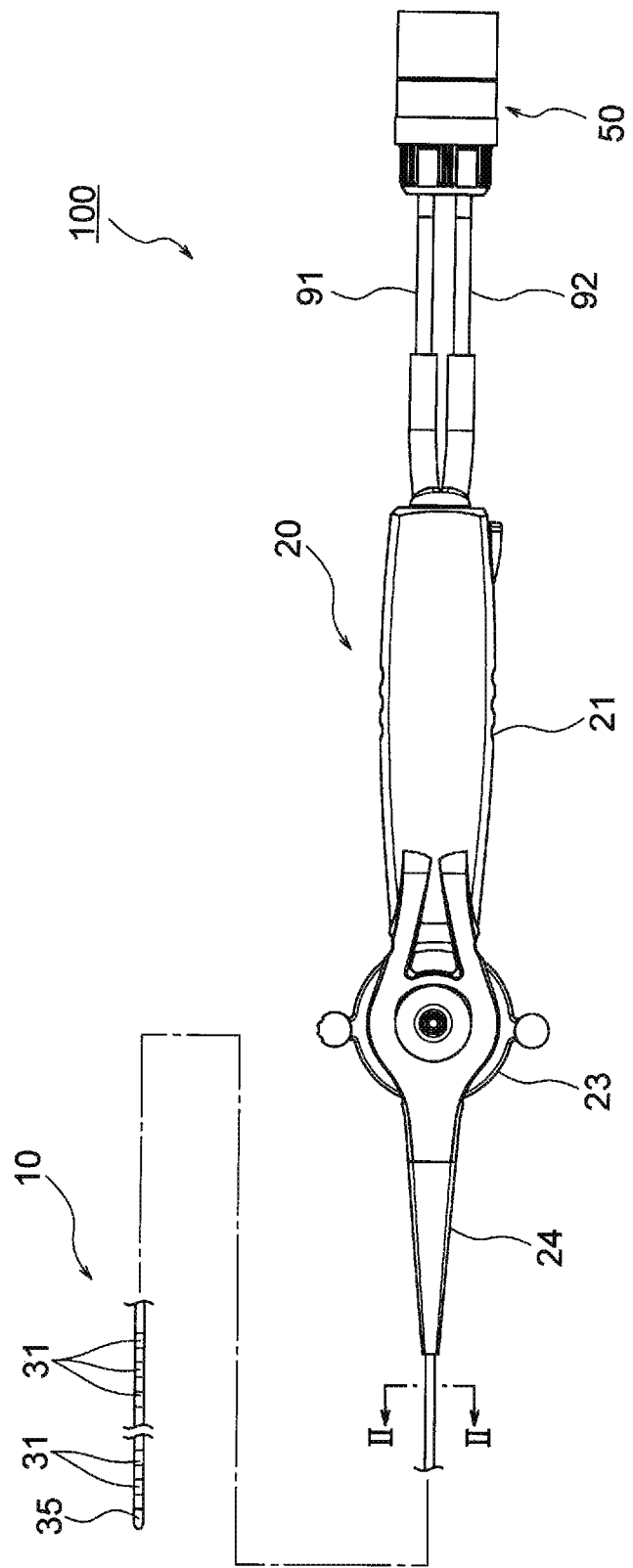
FIG. 1 is a plan view illustrating an electrode catheter according to a first embodiment of the present invention.

Hereinafter, embodiments of the present invention will be described with reference to the drawings. The present invention is not limited to these embodiments. In the present invention, "proximal end portion" refers to a portion that includes a proximal end and that has a certain length, and "distal end portion" refers to a portion that includes a distal end and that has a certain length.

First Embodiment

An electrode catheter 100 according to the present embodiment, illustrated in FIGS. 1 to 5 (FIGS. 5A and 5B), is an electrode catheter that is used to diagnose or treat arrhythmia. The electrode catheter 100 includes: an insulating tube member 10 that has a flexible portion at a distal end thereof and in which eight lumens 101 to 108, which are arranged at equal angular intervals along the circumferential direction, are formed; a handle 20 that is attached to a proximal end portion 12 of the tube member 10 and that includes a handle body 21 and a rotational operation portion 23 including wire fasteners 231 and 232; twenty ring-shaped electrodes 31 that are attached to an outer periphery of a distal end part of the tube member 10 (illustration of some of which is omitted in FIG. 1); a distal end tip 35 that is attached to a distal end of the tube member 10; twenty lead wires 41 whose distal ends are respectively connected to the twenty electrodes 31 and that extend in an inside of the tube member 10 along the axial direction; an electrode connector 50 that is disposed on a proximal end side of the handle 20 and that has terminals (not shown) to which proximal ends of the lead wires 41 are respectively connected; and operating wires 71 and 72 a distal end of each of which is fixed to a distal end portion of the tube member 10, that extend in the inside (the lumen) of the tube member 10 along the axial direction, and whose proximal ends are operable to be pulled.

The operating wires 71 and 72 respectively extend in the lumens 101 and 105 of the tube member 10, and four or two lead wires 41 extend in each of the lumens 102 to 104 and 106 to 108.

The proximal end portion 12 of the tube member 10 is inserted from a distal end of the handle 20 to an inside of the handle 20, and extends in the inside of the handle 20 in the proximal end direction.

A proximal end 121 of the tube member 10 is located in the inside of the handle 20 on the proximal end side of the rotational operation portion 23.

Side holes 111 and 115 that respectively lead from the lumens 101 and 105 to an outer peripheral surface of the tube member 10 are formed in a pipe wall of the proximal end portion 12 of the tube member 10 on a distal end side of the wire fasteners 231 and 232 of the rotational operation portion 23 at circumferential-direction positions respectively corresponding to the lumens 101 and 105.

A proximal end portion of the operating wire 71, which extends in the lumen 101, passes through the side hole 111 and extends to the outside of the tube member 10 (the inside of the handle 20). The proximal end of the operating wire 71 is fixed to the wire fastener 231 of the rotational operation portion 23. A proximal end portion of the operating wire 72, which extends in the lumen 105, passes through the side hole 115 and extends to the outside of the tube member 10 (the inside of the handle 20). The proximal end of the operating wire 72 is fixed to the wire fastener 232 of the rotational operation portion 23.

A proximal end portion of each of the lead wires 41, which extend in the lumens 102 to 104 and 106 to 108, extends from the proximal end 121 of the tube member 10 to the outside of the tube member 10, and extends in the inside of the handle 20. The proximal end of each of the lead wires 41 is connected to a predetermined terminal of the electrode connector 50.

The electrode catheter 100 according to the present embodiment includes the tube member 10, the handle 20, the twenty electrodes 31, the twenty lead wires 41, the electrode connector 50, and the operating wires 71 and 72.

Figure 2:
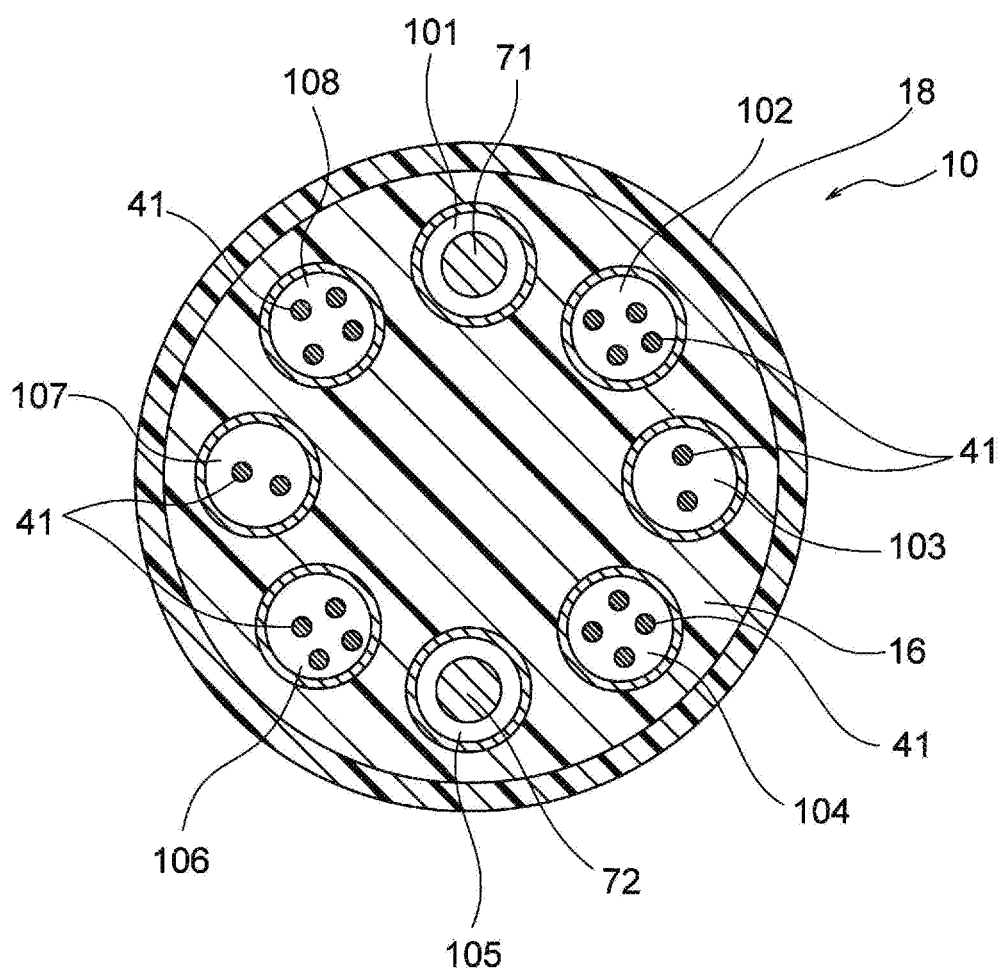
FIG. 2 is a cross-sectional view of a tube member that constitutes the electrode catheter illustrated in FIG. 1 (sectional view taken along line II-II of FIG. 1).

A distal end region of the tube member 10 is a flexible portion, and it is possible to flex the flexible portion by operating to rotate the rotational operation portion 23 described below. As illustrated in FIG. 2, in the tube member 10 that constitutes the electrode catheter 100, the eight lumens 101 to 108, which are arranged at equal angular intervals along the circumferential direction (45° intervals), are formed. In FIG. 2, a numeral 16 represents an inner (core) portion made of a low-rigidity nylon elastomer, and a numeral 18 represents an outer (shell) portion made of a high-rigidity nylon elastomer.

The lumens 101 to 108 are respectively defined and formed by lumen tubes made of a fluororesin or the like. Examples of a fluororesin that constitutes the lumen tube include perfluoroalkyl vinyl ether copolymer (PFA), polytetrafluoroethylene (PTFE), and the like.

As a nylon elastomer that constitutes the outer portion 18 of the tube member 10, an elastomer whose rigidity differs in the axial direction is used. Thus, the tube member 10 is structured so that the rigidity thereof increases stepwise from the distal end side toward the proximal end side. Moreover, a braid may be formed between the inner portion 16 and the outer portion 18 on the proximal end side of the tube member 10.

The handle 20 that constitutes the electrode catheter 100 is attached to the proximal end portion 12 of the tube member 10. The handle 20 includes the handle body 21, the rotational operation portion 23 including the wire fasteners 231 and 232, and a strain relief 24. By operating to rotate the rotational operation portion 23 (operating to pull the operating wire 71 or the operating wire 72), the flexible portion of the tube member 10 flexes, and it is possible to deflect the distal end of the tube member 10 in one direction or in the other direction.

The twenty ring-shaped electrodes 31 are attached to the distal end part of the tube member 10. In FIG. 1, illustration of some of the electrodes 31 is omitted. The electrodes 31 that constitute the electrode catheter 100 are connected, for example, to an electrocardiograph via the lead wires 41 and the electrode connector 50. Examples of the material of the electrodes 31 include metals having high electroconductivity, such as aluminum, copper, stainless steel, gold, platinum, and the like.

The distal end tip 35 is attached to the distal end of the tube member 10. A lead wire is not connected to the distal end tip 35, and the distal end tip 35 is not used as an electrode. However, the distal end tip 35 may be used as an electrode (a distal end electrode). Examples of the material of the distal end tip 35 include various resins and metals.

The distal ends of the lead wires 41 are respectively connected to the twenty electrodes 31. The twenty lead wires 41 that constitute the electrode catheter 100 are each welded to an inner peripheral surface of the electrodes 31 at the distal end thereof, enter the inside of the tube member 10 from side holes formed in the pipe wall of the tube member 10, and extend in the inside of the tube member 10 (the lumens 102 to 104 and 106 to 108) along the axial direction.

As illustrated in FIG. 2, four lead wires 41 extend in each of the lumens 102, 104, 106, and 108; and two lead wires 41 extend in each of the lumens 103 and 107. With the lead wires 41, it is possible to connect each of the electrodes 31 to an electrocardiograph.

The lead wires 41 are made from resin-coated wires in which outer peripheral surfaces of conductive metal wires are coated with a resin such as polyimide. Here, the thickness of the coating resin is about 2 to 30 μm.

In FIG. 1, a numeral 50 represents an electrode connector, which is disposed on the proximal end side (the outside) of the handle. A plurality of terminals (not shown) are disposed in an inside of the electrode connector 50. In the figure, numerals 91 and 92 respectively represent outer cords that guide the lead wires 41, which extend in the inside of the handle 20, to the electrode connector 50.

Figure 4A:
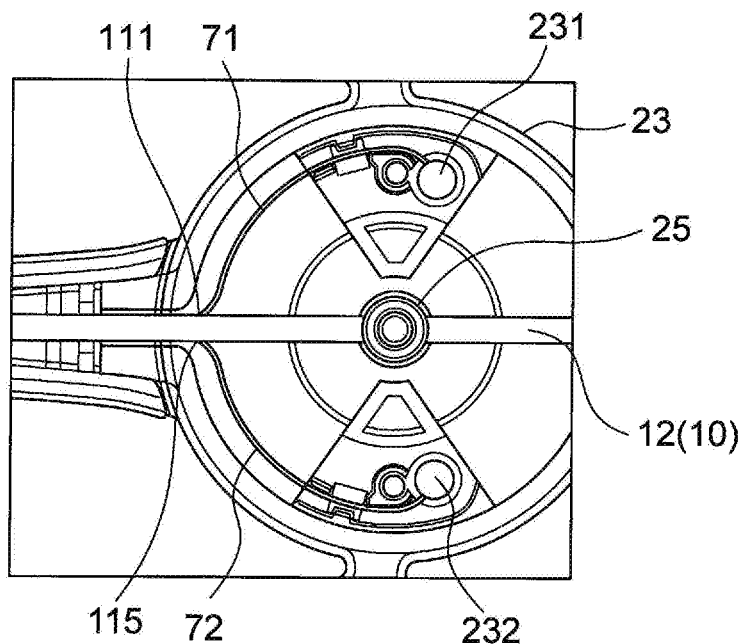
FIG. 4A is a partial enlarged view illustrating the inside of the handle illustrated in FIG. 3 (detailed view of a portion IV of FIG. 3).
Figure 4B:
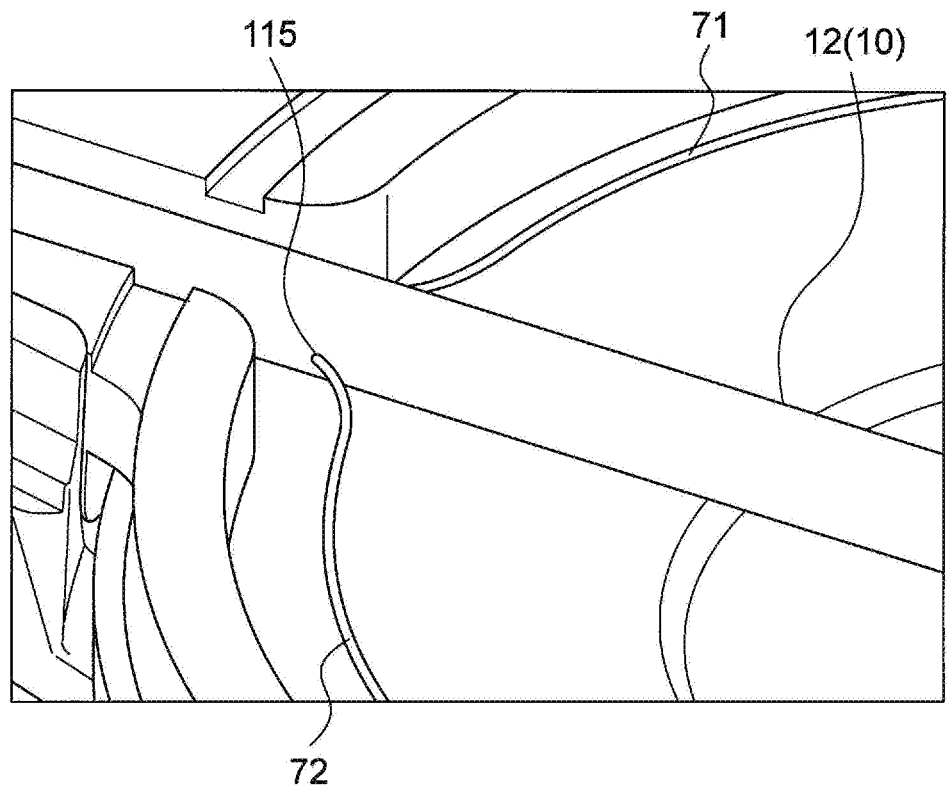
FIG. 4B is a partial enlarged view (perspective view) illustrating the inside of the handle illustrated in FIG. 3.

In FIGS. 2 to 4 (FIGS. 4A and 4B), numerals 71 and 72 represent operating wires. Distal ends of the operating wires 71 and 72 are respectively fixed to positions in the distal end portion of the tube member 10 that face each other (circumferential-direction positions in the tube member 10).

The operating wires 71 and 72 extend in the inside of the tube member 10 along the axial direction. As illustrated in FIG. 2, the operating wire 71 extends in the lumen 101 of the tube member 10, and the operating wire 72 extends in the lumen 105.

The operating wires 71 and 72 are made of a stainless steel or a Ni—Ti-based superelastic alloy material. However, it is not necessary that the operating wires 71 and 72 be made of a metal. The operating wire 71 may be made of, for example, a high-strength unconducive wire.

The lead wires 41 do not extend in the lumens 101 and 105, in which the operating wires 71 and 72 extend. Thus, when the rotational operation portion 23 is operated to rotate (when the operating wire 71 or the operating wire 72 is operated to be pulled), the lead wires 41, which extend in the inside of the tube member 10 (the lumens 102 to 104 and 106 to 108), are not damaged (for example, abraded) by the operating wires 71 and 72 that move in the axial direction.

As illustrated in FIG. 3, the proximal end portion 12 of the tube member 10 is inserted from the distal end of the handle 20 to the inside of the handle 20, and extends in the inside of the handle 20 in the proximal end direction beyond the rotational operation portion 23. Accordingly, the proximal end 121 of the tube member 10 is located on the proximal end side of the rotational operation portion 23. In the figure, a numeral 25 represents an adjustment pin that is fixed to the handle body 21 at the rotation center of the rotational operation portion 23. A through-hole into which the tube member 10 can be inserted is formed in the adjustment pin 25.

As illustrated in FIGS. 3 and 4 (FIGS. 4A and 4B), in the pipe wall of the proximal end portion 12 of the tube member 10 that extends in the inside of the handle 20, the side hole 111 that leads from the lumen 101 to the outer peripheral surface of the tube member 10 is formed at a circumferential-direction position in the tube member 10 that is on the distal end side of the wire fastener 231 of the rotational operation portion 23 and that corresponds to the lumen 101; and the side hole 115 that leads from the lumen 105 to the outer peripheral surface of the tube member 10 is formed at a circumferential-direction position in the tube member 10 that is on the distal end side of the wire fastener 232 of the rotational operation portion 23 and that corresponds to the lumen 105.

A proximal end portion of the operating wire 71, which extends in the lumen 101 of the tube member 10, passes through the side hole 111 and extends to the outside of the tube member 10 (the inside of the handle 20). The proximal end of the operating wire 71 is fixed to the wire fastener 231 of the rotational operation portion 23 of the handle 20. Moreover, a proximal end portion of the operating wire 72, which extends in the lumen 105 of the tube member 10, passes through the side hole 115 and extends to the outside of the tube member 10 (the inside of the handle 20). The proximal end of the operating wire 72 is fixed to the wire fastener 232 of the rotational operation portion 23 of the handle 20. By operating the rotational operation portion 23, the operating wire 71 or the operating wire 72 is pulled, and thereby the distal end of the tube member 10 is deflected in one direction or in the other direction.

Figure 5A:
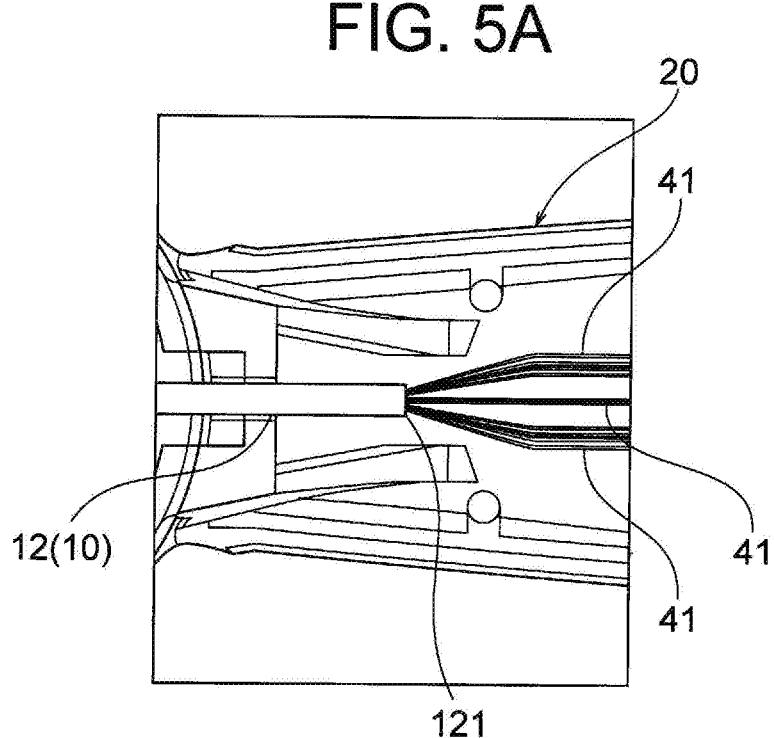
FIG. 5A is a partial enlarged view illustrating the inside of the handle illustrated in FIG. 3 (detailed view of a portion V of FIG. 3).
Figure 5B:
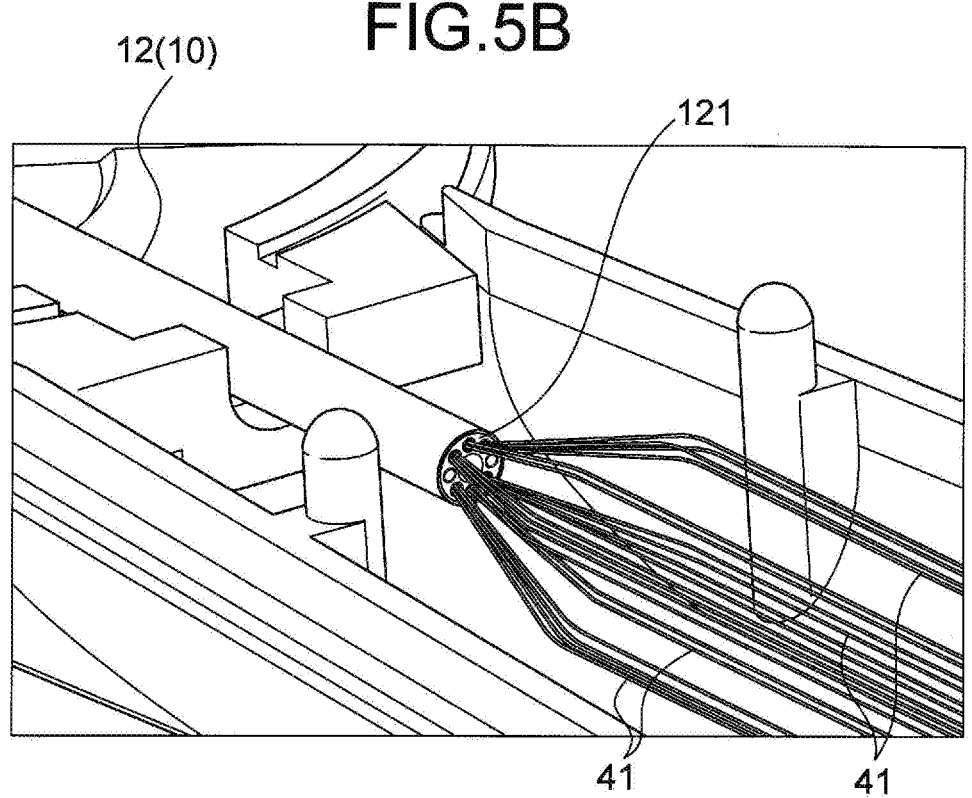
FIG. 5B is a partial enlarged view (perspective view) illustrating the inside of the handle illustrated in FIG. 3.

As illustrated in FIGS. 3 and 5 (FIGS. 5A and 5B), a proximal end portion of each of the lead wires 41, which respectively extend in the lumens 102 to 104 and 106 to 108 of the tube member 10, extends from the proximal end 121 of the tube member 10 to the outside of the tube member 10 (the inside of the handle 20).

The proximal end portion of each of the lead wires 41, which extends to the outside of the tube member 10 (the inside of the handle 20), extends in the inside of the handle 20 further in the proximal end direction, extends to the outside of the handle 20, and is guided to the vicinity of the electrode connector 50 by extending in the inside of the outer cord 91 or the outer cord 92. The proximal end of each of the lead wires 41 is connected to a predetermined terminal of the electrode connector 50.

With the electrode catheter 100 according to the present embodiment, the proximal end portion 12 of the tube member 10, which is inserted to the inside of the handle 20 from the distal end of the handle 20, extends in the inside of the handle 20 in the proximal end direction beyond the rotational operation portion 23, and the proximal end 121 of the tube member 10 is located on the proximal end side of the rotational operation portion 23. Thus, at least a part of each of the lead wires 41 in the inside of the handle 20 that is located in a region from the distal end of the handle 20 to the proximal end of the rotational operation portion 23 is protected by the tube member 10. Therefore, when the rotational operation portion 23 is operated to rotate, each of the lead wires 41 does not receive interference from the rotational operation portion 23 and the operating wires 71 and 72.

Moreover, the proximal end portion of each of the lead wires 41, which extends out from the proximal end 121 of the tube member 10 located on the proximal end side of the rotational operation portion 23, does not receive interference from the rotational operation portion 23 and the operating wires 71 and 72.

Moreover, the proximal end portions of the operating wires 71 and 72 are caused to pass through the side holes 111 and 115, which are formed in the proximal end portion 12 of the tube member 10, and to extend to the outside of the tube member 10 (the inside of the handle 20). Therefore, although the proximal end portion 12 of the tube member 10 extends in the proximal end direction beyond the rotational operation portion 23, it is possible to fix the proximal ends of the operating wires 71 and 72 to the wire fasteners 231 and 232 of the rotational operation portion 23.

Moreover, the proximal end portion of each of the lead wires 41, which extends to the outside of the tube member 10 (the inside of the handle 20), extends in the inside of the handle 20 further in the proximal end direction, extends to the outside of the handle 20, and is guided to the vicinity of the electrode connector 50 by the outer cord 91 or the outer cord 92. Therefore, it is possible to reliably connect the proximal end of each of the lead wires 41 to a predetermined terminal of the electrode connector 50.

Second Embodiment

An electrode catheter 200 according to the present embodiment, illustrated in FIGS. 6 to 11, is an electrode catheter that has a guide wire lumen and that is used to diagnose or treat arrhythmia. The electrode catheter 200 includes: an insulating tube member 15 that has a flexible portion at a distal end thereof and in which a central lumen 150, which serves as a guide wire lumen, and eight sub-lumens 151 to 158, which are arranged at equal angular intervals around the central lumen 150, are formed; a handle 20 that is attached to a proximal end portion 17 of the tube member 15 and that includes a handle body 21 and a rotational operation portion 23 including wire fasteners 231 and 232; twenty ring-shaped electrodes 31 that are attached to an outer periphery of a distal end part of the tube member 15 (illustration of some of which is omitted in FIG. 6); a distal end tip 37 that is attached to a distal end of the tube member 15; twenty lead wires 41 whose distal ends are respectively connected to the twenty electrodes 31 and that extend in an inside of the tube member 15 along the axial direction; an electrode connector 50 that is disposed on a proximal end side of the handle 20 and that has terminals (not shown) to which proximal ends of the lead wires 41 are respectively connected; a guide wire connector 60 that is disposed on the proximal end side of the handle 20 and that has a guide wire port 61 at a proximal end thereof; and operating wires 71 and 72 a distal end of each of which is fixed to the distal end portion of the tube member 15, that extend in the inside of the tube member 15 along the axial direction, and whose proximal ends are operable to be pulled.

The operating wires 71 and 72 respectively extend in the sub-lumens 151 and 155 of the tube member 15, and four or two the lead wires 41 extend in each of the sub-lumens 152 to 154 and 156 to 158.

The proximal end portion 17 of the tube member 15 is inserted from a distal end of the handle 20 to the inside of the handle 20, extends in the inside of the handle 20, and extends from a proximal end portion 202 of the handle 20 to the outside of the handle 20. The guide wire connector 60 is connected to a proximal end of the tube member 15 located outside of the handle 20. Thus, the central lumen 150 of the tube member 15 and the guide wire port 61 of the guide wire connector 60 communicate.

In the proximal end portion 17 of the tube member 15, on the distal end side of the wire fasteners 231 and 232 of the rotational operation portion 23, first side holes 161 and 165, which respectively lead from the sub-lumens 151 and 155 to an outer peripheral surface of the tube member 15, are formed at circumferential-direction positions respectively corresponding to the sub-lumens 151 and 155; and, on the proximal end side of the rotational operation portion 23, second side holes 162 to 164 and 166 to 168, which respectively lead from the sub-lumens 152 to 154 and 156 to 158 to the outer peripheral surface of the tube member 15, are formed at circumferential-direction positions respectively corresponding to the sub-lumens.

A proximal end portion of the operating wire 71, which extends in the sub-lumen 151, passes through the first side hole 161 and extends to the outside of the tube member 15 (the inside of the handle 20). The proximal end of the operating wire 71 is fixed to the wire fastener 231 of the rotational operation portion 23. A proximal end portion of the operating wire 72, which extends in the sub-lumen 155, passes through the first side hole 165 and extends to the outside of the tube member 15 (the inside of the handle 20). The proximal end of the operating wire 72 is fixed to the wire fastener 232 of the rotational operation portion 23.

Proximal end portions of the lead wires 41, which extend in the sub-lumens 152 to 154 and 156 to 158, respectively pass through the second side holes 162 to 164 and 166 to 168 and extend to the outside of the tube member 15, and the proximal end of each of the lead wires 41 is connected to a predetermined terminal of the electrode connector 50.

The electrode catheter 200 according to the present embodiment includes the tube member 15, the handle 20, the twenty electrodes 31, the twenty lead wires 41, the electrode connector 50, the guide wire connector 60, and the operating wires 71 and 72.

In the electrode catheter 200 according to the present embodiment illustrated in FIGS. 6 to 11, constituent elements that are the same as those of the electrode catheter 100 according to the first embodiment are denoted by numerals that are the same as those in FIGS. 1 to 5, and descriptions of such constituent elements are omitted.

A distal end region of the tube member 15 is a flexible portion, and it is possible to flex the flexible portion by operating to rotate the rotational operation portion 23 described below.

Figure 7:
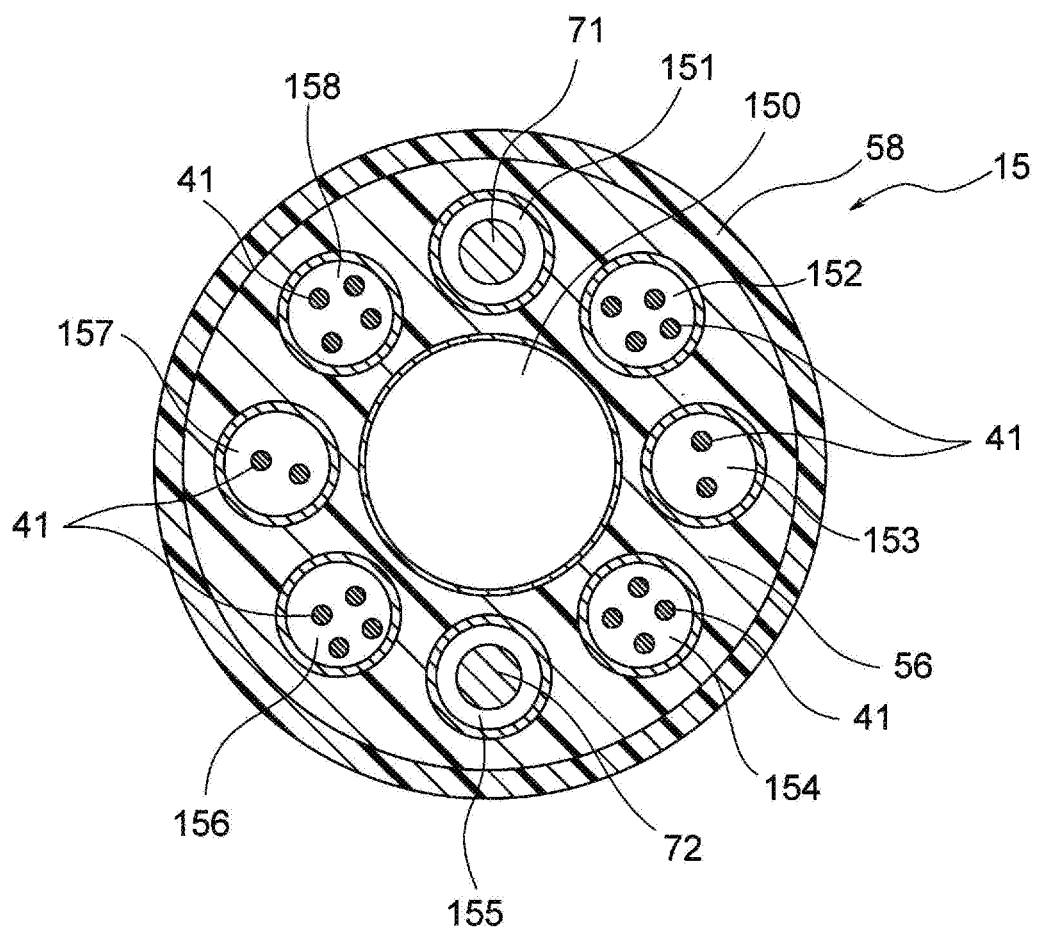
FIG. 7 is a cross-sectional view of a tube member that constitutes the electrode catheter illustrated in FIG. 6 (sectional view taken along line VII-VII of FIG. 6).

As illustrated in FIG. 7, in the tube member 15 that constitutes the electrode catheter 200, the central lumen 150, which serves as a guide wire lumen, and the eight lumens 151 to 158, which are arranged around the central lumen 150 at equal angular intervals along the circumferential direction (45° intervals), are formed. In the figure, a numeral 56 represents an inner (core) portion made of a low-rigidity nylon elastomer, and a numeral 58 represents an outer (shell) portion made of a high-rigidity nylon elastomer. The lumens 151 to 158 are respectively defined and formed by lumen tubes made of a fluororesin or the like.

The distal end tip 37 is attached to the distal end of the tube member 15. The distal end tip 37 has a lumen that communicates with or that is common to the central lumen 150 of the tube member 15, and the distal end of the distal end tip 37 is open. A lead wire is not connected to the distal end tip 37, and the distal end tip 37 is not used as an electrode in the present embodiment. Examples of the material of the distal end tip 37 include various resins and metals.

The twenty lead wires 41 that constitute the electrode catheter 200 are respectively welded to an inner peripheral surface of the electrodes 31 at the distal ends thereof, enter the inside of the tube member 15 from side holes formed in the pipe wall of the tube member 15, and extend in the inside of the tube member 15 (the lumens 152 to 154 and 156 to 158) along the axial direction.

As illustrated in FIG. 7, four lead wires 41 extend in each of the lumens 152, 154, 156, and 158; and two lead wires 41 extend in each of the lumens 153 and 157.

Distal ends of the operating wires 71 and 72 are respectively fixed to positions in the distal end portion of the tube member 15 that face each other (circumferential-direction positions in the tube member 15).

The operating wires 71 and 72 extend in the inside of the tube member 15 along the axial direction. As illustrated in FIG. 7, the operating wire 71 extends in the lumen 151 of the tube member 15, and the operating wire 72 extends in the lumen 155.

Figure 8:
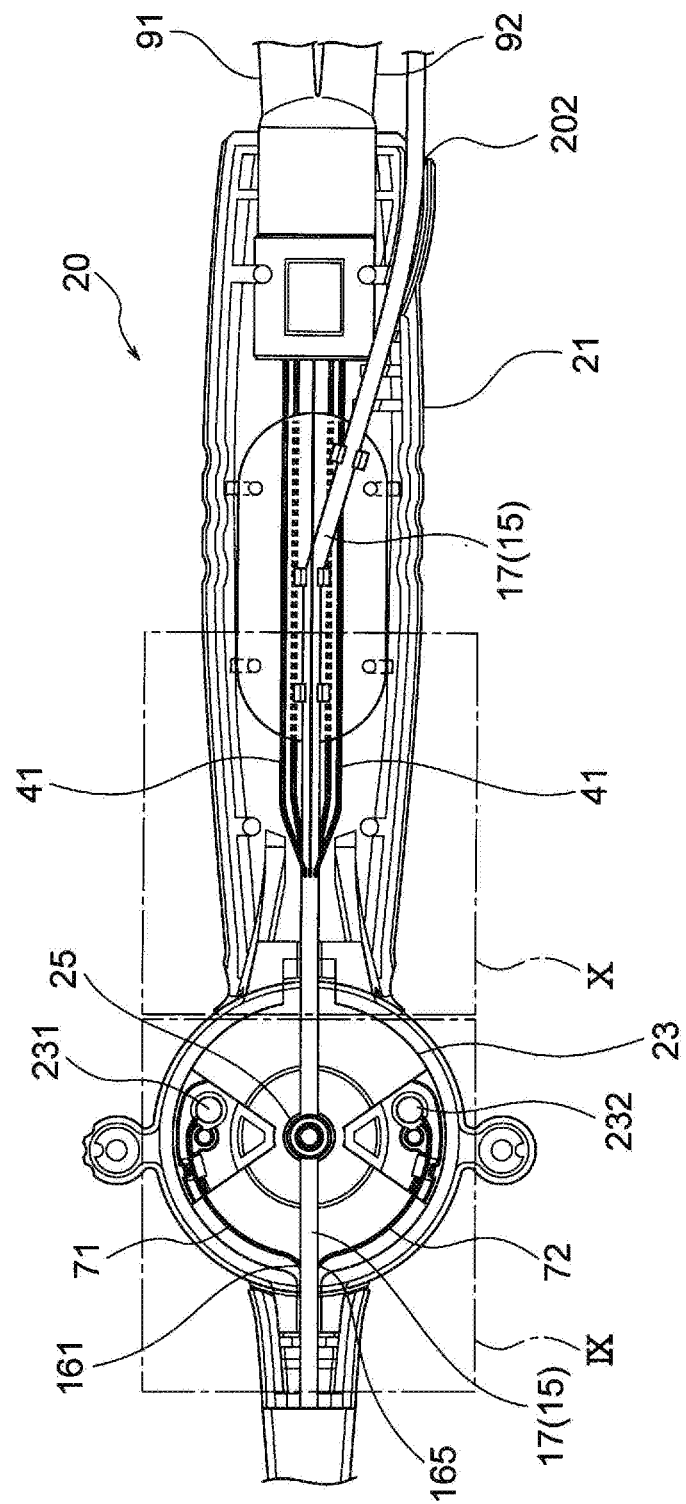
FIG. 8 is a plan view illustrating an inside of a handle that constitutes the electrode catheter illustrated in FIG. 6.

As illustrated in FIG. 8, the proximal end portion 17 of the tube member 15 is inserted from the distal end of the handle 20 to the inside of the handle 20, extends in the inside of the handle 20 in the proximal end direction, passes an axial-direction position where the rotational operation portion 23 is disposed, and extends to the outside of the handle 20 from the proximal end portion 202 of the handle 20.

Figure 6:
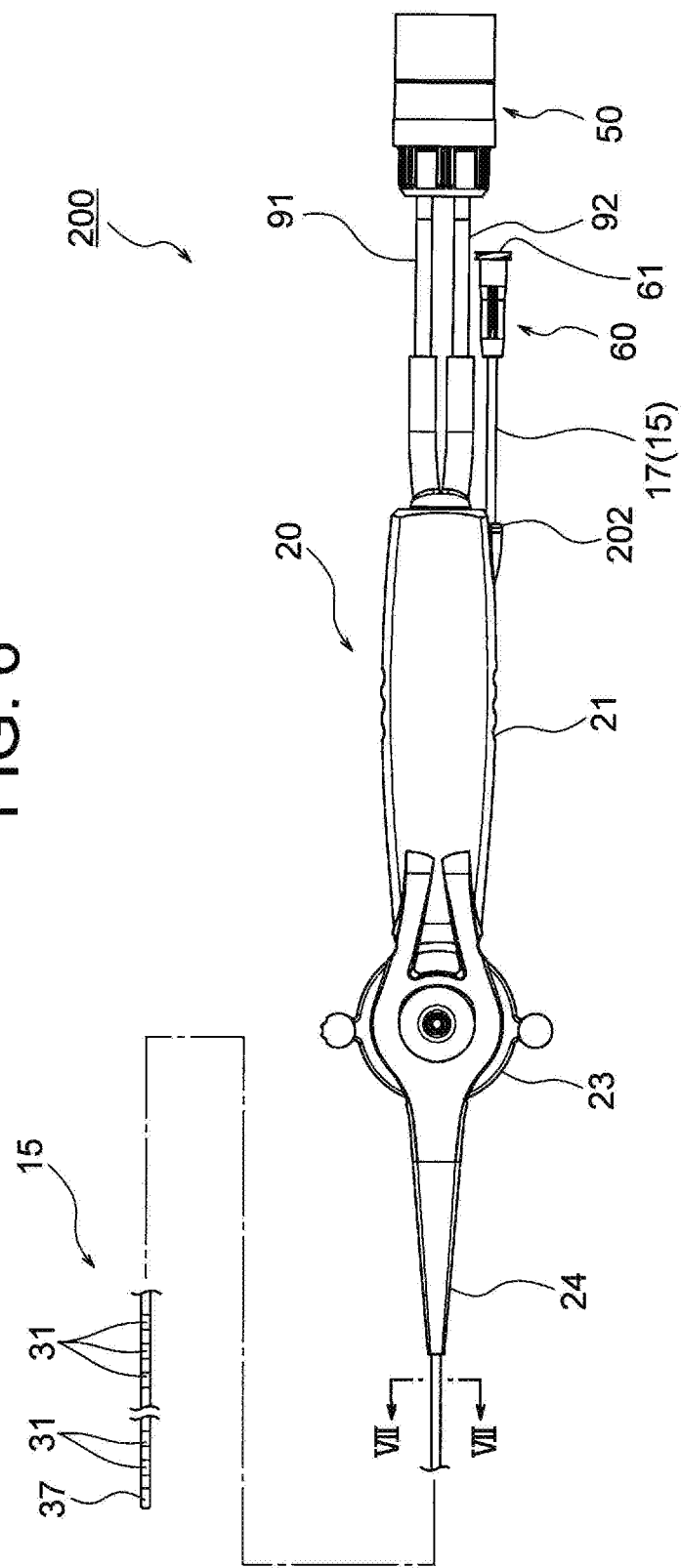
FIG. 6 is a plan view illustrating an electrode catheter according to a second embodiment of the present invention.

As illustrated in FIG. 6, the guide wire connector 60 is connected to a proximal end of the tube member 15 (the proximal end portion 17), which extends to the outside of the handle 20. Thus, the central lumen 150 of the tube member 15 and the guide wire port 61 of the guide wire connector 60 communicate. With such a structure, an insertion path of a guide wire that leads from the guide wire port 61 of the guide wire connector 60 to a distal end opening of the central lumen 150 (the guide wire lumen) of the tube member 15 is reliably maintained.

Figure 9A:
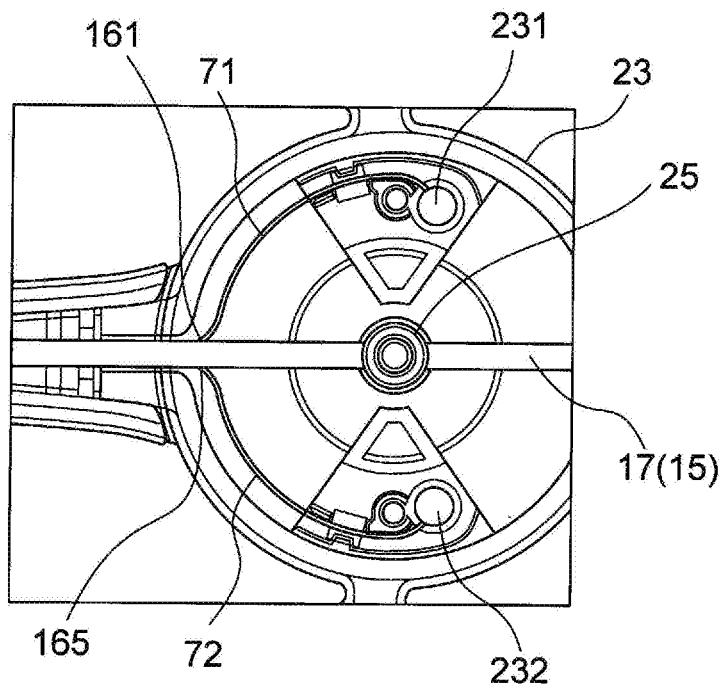
FIG. 9A is a partial enlarged view illustrating the inside of the handle illustrated in FIG. 8 (detailed view of a portion IX of FIG. 8).
Figure 9B:
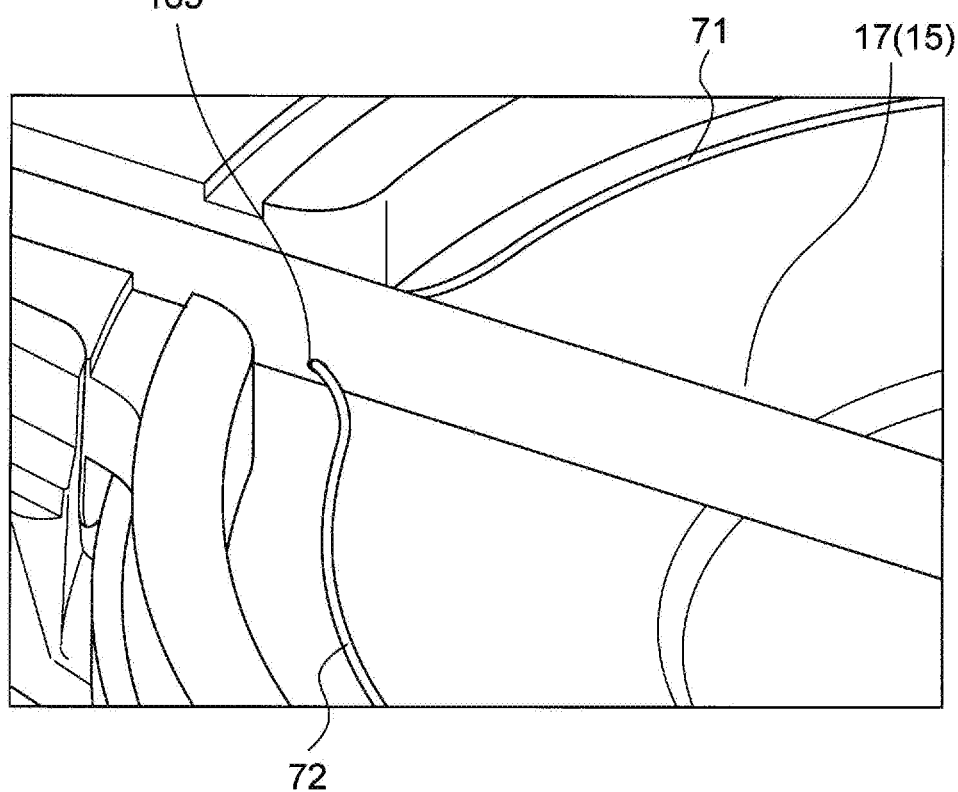
FIG. 9B is a partial enlarged view (perspective view) illustrating the inside of the handle illustrated in FIG. 8.

As illustrated in FIGS. 8 and 9 (FIGS. 9A and 9B), in the pipe wall of the proximal end portion 17 of the tube member 15 that extends in the inside of the handle 20, the first side hole 161 that leads from the sub-lumen 151 to the outer peripheral surface of the tube member 15 is formed at a circumferential-direction position in the tube member 15 that is on the distal end side of the wire fastener 231 of the rotational operation portion 23 and that corresponds to the sub-lumen 151; and the first side hole 165 that leads from the sub-lumen 155 to the outer peripheral surface of the tube member 15 is formed at a circumferential-direction position in the tube member 15 that is on the distal end side of the wire fastener 232 of the rotational operation portion 23 and that corresponds to the sub-lumen 155.

A proximal end portion of the operating wire 71, which extends in the sub-lumen 151 of the tube member 15, passes through the first side hole 161 and extends to the outside of the tube member 15 (the inside of the handle 20). The proximal end of the operating wire 71 is fixed to the wire fastener 231 of the rotational operation portion 23 of the handle 20. Moreover, a proximal end portion of the operating wire 72, which extends in the sub-lumen 155 of the tube member 15, passes through the first side hole 165 and extends to the outside of the tube member 15 (the inside of the handle 20). The proximal end of the operating wire 72 is fixed to the wire fastener 232 of the rotational operation portion 23 of the handle 20. By operating the rotational operation portion 23, the operating wire 71 or the operating wire 72 is pulled, and thereby the distal end of the tube member 15 is deflected in one direction or in the other direction.

Figure 10:
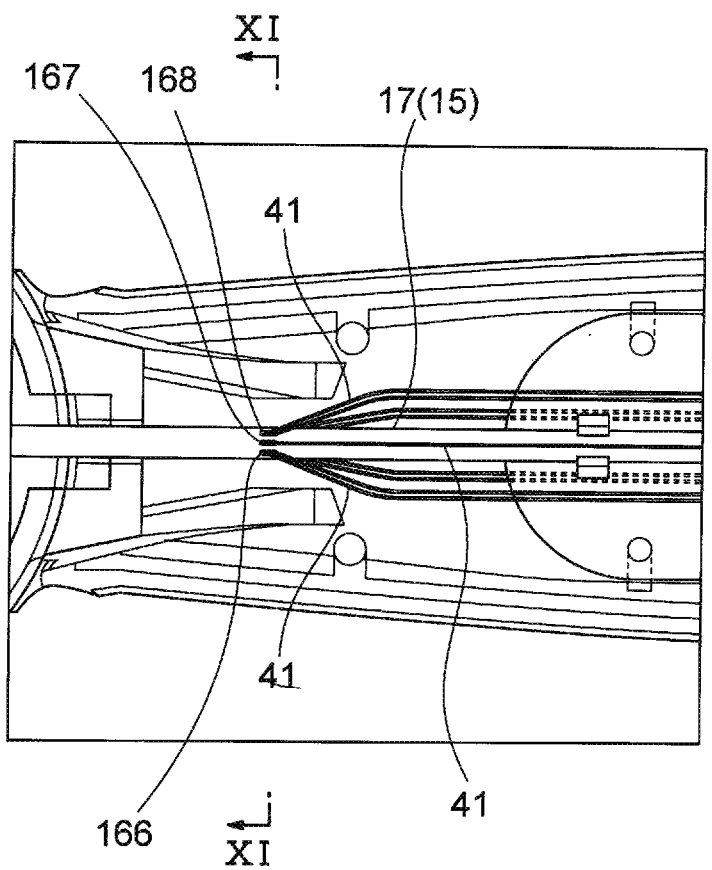
FIG. 10 is a partial enlarged view illustrating the inside of the handle illustrated in FIG. 8 (detailed view of a portion X of FIG. 8).
Figure 11:
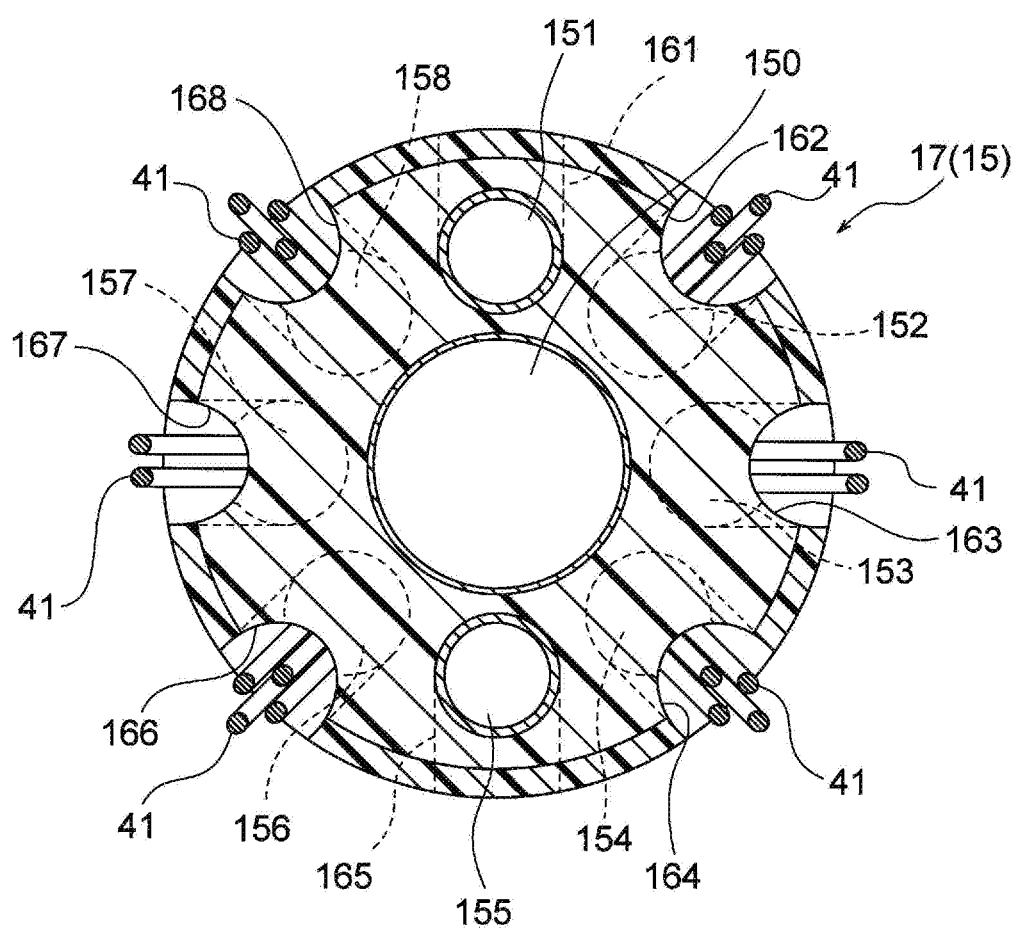
FIG. 11 is a cross-sectional view of a tube member that constitutes the electrode catheter illustrated in FIG. 6 (sectional view taken along line XI-XI of FIG. 10).

As illustrated in FIGS. 8, 10, and 11, in the pipe wall of the proximal end portion 17 of the tube member 15 that extends in the inside of the handle 20, the second side holes 162 to 164 and 166 to 168 that respectively lead from the sub-lumens to the outer peripheral surface of the tube member 15 are formed at circumferential-direction positions in the tube member 15 that are on the proximal end side of the rotational operation portion 23 and that respectively correspond to the sub-lumens 152 to 154 and 156 to 158.

Proximal end portions of the lead wires 41, which extend in the sub-lumens 152 to 154 and 156 to 158, respectively pass through the second side holes 162 to 164 and 166 to 168 and extend to the outside of the tube member 15 (the inside of the handle 20).

The proximal end portion of each of the lead wires 41, which extends to the outside of the tube member 15 (the inside of the handle 20), extends in the inside of the handle 20 further in the proximal end direction, extends to the outside of the handle 20, and is guided to the vicinity of the electrode connector 50 by extending in the inside of the outer cord 91 or the outer cord 92. The proximal end of each of the lead wires 41 is connected to a predetermined terminal of the electrode connector 50.

With the electrode catheter 200 according to the present embodiment, the guide wire connector 60 is connected to the proximal end of the tube member 15, which is located outside of the handle 20, and it is possible to reliably maintain an insertion path of a guide wire that leads from the port 61 of the guide wire connector 60 to a distal end opening of the central lumen 150 (the guide wire lumen) of the tube member 15. Therefore, it is possible to insert the electrode catheter 200 to a target region along the guide wire.

Moreover, the proximal end portion 17 of the tube member 15, which is inserted to the inside of the handle 20 from the distal end of the handle 20, extends in the inside of the handle 20 in the proximal end direction, passes an axial-direction position where the rotational operation portion 23 is disposed, and extends to the outside of the handle 20 from the proximal end portion 202 of the handle 20. Thus, each of the lead wires 41 in the inside of the handle 20 is protected by the tube member 15. Therefore, when the rotational operation portion 23 is operated to rotate, the lead wires 41 do not receive interference from the rotational operation portion 23 and the operating wires 71 and 72.

Moreover, the proximal end portions of the operating wires 71 and 72 are caused to pass through the side holes 161 and 165, which are formed in the proximal end portion 17 of the tube member 15, and to extend to the outside of the tube member 15 (the inside of the handle 20). Therefore, although the proximal end of the tube member 15 is located outside of the handle 20, it is possible to fix the proximal ends of the operating wires 71 and 72 to the wire fasteners 231 and 232 of the rotational operation portion 23.

Moreover, the proximal end portion of each of the lead wires 41 is caused to pass through one of the second side holes 162 to 164 and 166 to 168, which are formed in the proximal end portion 17 of the tube member 15, and to extend to the outside of the tube member 15. Therefore, although the proximal end portion 17 of the tube member 15 extends to the outside of the handle 20, it is possible to cause the proximal end portion of each of the lead wires 41 to extend out to the inside of the handle 20.

Moreover, the second side holes 162 to 164 and 166 to 168, for causing the proximal end portions of the lead wires 41 to extend out, are formed in the pipe wall of the proximal end portion 17 of the tube member 15 on the proximal end side of the rotational operation portion 23. Therefore, when the rotational operation portion 23 is operated, the proximal end portions of the lead wires 41, which respectively extend out from the second side holes, do not receive interference from the rotational operation portion 23 and the operating wires 71 and 72.

Moreover, the proximal end portion of each of the lead wires 41, which extends out to the inside of the handle 20, extends in the inside of the handle 20, extends to the outside of the handle 20, and is guided by the outer cord 91 or the outer cord 92 to the vicinity of the electrode connector 50. Therefore, it is possible to reliably connect the proximal end of each of the lead wires 41 to a predetermined terminal of the electrode connector 50.

Moreover, the tube member 15, whose proximal end portion 17 extends in the inside of the handle 20, is a member that constitutes a catheter shaft on the distal end side of the handle 20 and has high strength. Therefore, when the rotational operation portion 23 is operated, even if the tube member 15 receives interference from the rotational operation portion 23, the operating wires 71 and 72, and the lead wires 41, the proximal end portion 17 of the tube member 15 does not kink and the lumen does not collapse (the insertion characteristics of the guide wire are not impaired).

Heretofore, embodiments of the present invention have been described. The present invention is not limited to these embodiments and can be modified in various ways.

For example, an operation mechanism for deflecting the distal end of the tube member is not limited to the rotational operation portion described above. It is possible to use various operation mechanisms that are included in existing known catheter handles, such as a mechanism that deflects the distal end by moving an operation portion in an axial (front-back) direction and a mechanism that deflects the distal end by rotating an operation portion around an axis, as "an operation mechanism for a distal-end deflecting operation".

Moreover, in the case where the proximal end portion of the lead wire is caused to extend to the outside of the handle, it is not necessary to cause the proximal end portion to extend out from the proximal end of the handle (a position to which the outer cord is connected in the embodiments described above). The proximal end portion of the lead wire may be caused to extend out from a middle portion (a side surface) of the handle on the proximal end side of the rotational operation portion.

Moreover, in the second embodiment, it is not necessary to cause the proximal end portion of the tube member to extend out from the proximal end portion (202) of the handle. The proximal end portion of the tube member may be caused to extend out from a middle portion (a side surface) of the handle on the proximal end side of the rotational operation portion or the proximal end of the handle (a position to which the outer cord is connected in the second embodiment). Here, as a modification of the second embodiment, the proximal end portion of the lead wire may be caused to extend out from a middle portion of the handle, and the proximal end portion of the tube member may be caused to extend out from the proximal end of the handle.

Moreover, as a modification in which the proximal end portion of the lead wire does not extend to the outside of the handle, an electrode connector to which the proximal end of the lead wire is fixed may be incorporated in the handle.

Moreover, in the second embodiment, by connecting a liquid injection pipe to the proximal end of tube member, the central lumen may be used as an irrigation lumen.

With such an electrode catheter, the liquid injection pipe is connected to the proximal end of the tube member that is located outside of the handle. Therefore, it is possible to reliably maintain a liquid flow path that leads from the injection pipe to the irrigation lumen of the tube member. Thus, it is possible to irrigate the distal end electrode (a distal end tip used as an electrode) and the like with a liquid from the injection pipe.

REFERENCE SIGNS LIST

100 electrode catheter
10 tube member
101 to 108 lumen
111, 115 side hole
12 proximal end portion of tube member
121 proximal end of tube member
16 inner (core) portion
18 outer (shell) portion
20 handle
21 handle body
23 rotational operation portion
231, 232 wire fastener
24 strain relief
25 adjustment pin
31 electrode
35 distal end tip
41 lead wire
50 electrode connector
71, 72 operating wire
56 inner (core) portion
58 outer (shell) portion
91, 92 outer cord

200 electrode catheter
15 tube member
150 central lumen
151 to 158 sub-lumen
161, 165 first side hole
162 to 164, 166 to 168 second side hole
17 proximal end portion of tube member
37 distal end tip
60 guide wire connector
61 guide wire port

The invention claimed is:

1. An electrode catheter, comprising:
an insulating tube member that has a flexible portion at a distal end thereof;
a handle that is attached to a proximal end portion of the tube member and that includes an operation mechanism for a distal-end deflecting operation;
at least one electrode that is attached to the distal end and/or an outer periphery of a distal end part of the tube member;
at least one lead wire whose distal end is connected to the electrode and that extends in an inside of the tube member along an axial direction;
an electrode connector that is disposed at an outside of the handle or is incorporated in the handle and that has a terminal to which a proximal end of the lead wire is connected; and
at least one operating wire whose distal end is fixed to the electrode attached to the distal end of the tube member or to a distal end portion of the tube member, that extends in the inside of the tube member along the axial direction, and that is operable to be pulled as a proximal end thereof is fixed to a constituent element of the operation mechanism,
wherein the proximal end portion of the tube member is inserted from a distal end of the handle to an inside of the handle, and extends in the inside of the handle in a proximal end direction beyond a fixing position on the constituent element of the operation mechanism where the proximal end of the operating wire is fixed, and extends to the outside of the handle,
wherein at least one first side hole that opens in an outer peripheral surface of the tube member is formed in a pipe wall of the proximal end portion of the tube member on a distal end side of the fixing position on the constituent element of the operation mechanism where the proximal end of the operating wire is fixed,
wherein the proximal end portion of the operating wire passes through the first side hole and extends to an outside of the tube member,
wherein at least one second side hole that opens in the outer peripheral surface of the tube member is formed in the pipe wall of a part of the proximal end portion of the tube member extending in the inside of the handle on a proximal end side of the fixing position on the constituent element of the operation mechanism where the proximal end of the operating wire is fixed, and
wherein a proximal end portion of the lead wire passes through the second side hole and extends to the outside of the tube member.

2. The electrode catheter according to claim 1,
wherein the operation mechanism is a rotational operation portion that includes a wire fastener and that is used for the distal-end deflecting operation,
wherein the proximal end of the operating wire is fixed to the wire fastener of the rotational operation portion, and wherein the proximal end portion of the tube member is inserted from the distal end of the handle to the inside of the handle and extends in the inside of the handle in the proximal end direction beyond the rotational operation portion.

3. The electrode catheter according to claim 1, wherein the tube member has a multi-lumen structure that includes a guide wire lumen, and wherein a guide wire connector that has a port that communicates with the guide wire lumen is connected to a proximal end of the tube member.

4. The electrode catheter according to claim 1, wherein the tube member has a multi-lumen structure that includes an irrigation lumen, and wherein a liquid injection pipe that communicates with the irrigation lumen is connected to a proximal end of the tube member.

* * * * *